United States Patent
Liu et al.

(10) Patent No.: US 12,129,299 B2
(45) Date of Patent: Oct. 29, 2024

(54) MUTANT ANTI-CTLA-4 ANTIBODIES WITH IMPROVED IMMUNOTHERAPEUTIC EFFECT BUT ATTENUATED ADVERSE EFFECTS

(71) Applicants: ONCOC4, INC., Rockville, MD (US); University of Maryland, Baltimore, Baltimore, MD (US)

(72) Inventors: Yang Liu, Baltimore, MD (US); Pan Zheng, Baltimore, MD (US); Fei Tang, Baltimore, MD (US); Mingyue Liu, Baltimore, MD (US); Martin Devenport, Gaithersburg, MD (US); Xuexiang Du, Baltimore, MD (US); Yan Zhang, Rockville, MD (US)

(73) Assignees: OncoC4, Inc., Rockville, MD (US); University of Maryland, Baltimore, Baltimore, MD (US)

( * ) Notice: Subject to any disclaimer, the term of this patent is extended or adjusted under 35 U.S.C. 154(b) by 1018 days.

(21) Appl. No.: 16/967,079

(22) PCT Filed: Jan. 29, 2019

(86) PCT No.: PCT/US2019/015686
§ 371 (c)(1),
(2) Date: Aug. 3, 2020

(87) PCT Pub. No.: WO2019/152423
PCT Pub. Date: Aug. 8, 2019

(65) Prior Publication Data
US 2021/0040212 A1 Feb. 11, 2021

Related U.S. Application Data

(60) Provisional application No. 62/754,781, filed on Nov. 2, 2018, provisional application No. 62/647,123, filed on Mar. 23, 2018, provisional application No. 62/625,662, filed on Feb. 2, 2018.

(51) Int. Cl.
*C07K 16/28* (2006.01)

(52) U.S. Cl.
CPC ...... *C07K 16/2818* (2013.01); *C07K 16/2827* (2013.01); *C07K 2317/565* (2013.01); *C07K 2317/71* (2013.01)

(58) Field of Classification Search
None
See application file for complete search history.

(56) References Cited

U.S. PATENT DOCUMENTS

| | | | |
|---|---|---|---|
| 10,787,518 B2 | 9/2020 | Bernett et al. | |
| 2003/0086930 A1 | 5/2003 | Mueller | |
| 2016/0243225 A1* | 8/2016 | Ioffe | C07K 14/71 |
| 2016/0244526 A1 | 8/2016 | Igawa et al. | |
| 2016/0340428 A1 | 11/2016 | Yang | |

FOREIGN PATENT DOCUMENTS

| | | | | |
|---|---|---|---|---|
| CN | 105636986 A | 6/2016 | | |
| EP | 1262193 | * 5/2002 | ......... | A61K 39/395 |
| JP | 2016-539096 | 12/2016 | | |
| WO | 2014089113 | 6/2014 | | |
| WO | 2017106372 | 6/2017 | | |
| WO | 2017120612 A1 | 7/2017 | | |
| WO | WO2017120612 | * 7/2017 | ............. | A61K 48/00 |

OTHER PUBLICATIONS

Schrörs et al., Front. Immunol. 14:1102282. doi: 10.3389/fimmu.2023.1102282 (Year: 2023).*
Du et al., J Immunol (2020) 204 (1_Supplement): 244.10 (Year: 2020).*
Jeffrey Weber, The Oncologist 2008;13(suppl 4):16-25 (Year: 2008).*
Karimi et al., Front. Oncol. 11:624780. doi: 10.3389/fonc.2021.624780 (Year: 2021).*
Bose CK., Indian J Med Paediatr Oncol 2017;38:182-9 (Year: 2017).*
Igawa et al., Biochimica et Biophysica Acta, 2014, 1844: 1943-1950 (Year: 2014).*
Singapore Patent Application No. 11202007017P; Search Report; Intellectual Property Office of Singapore dated Feb. 25, 2023.
Igawa, T., et. al., pH-dependent antigen-binding antibodies as a novel therapeutic modality; Biochimica et Biophysica Acta, Aug. 12, 2014, vol. 1844, No. 11, pp. 1943-1950.
International Search Report and Written Opinion regarding PCT/US2019/015686, dated May 31, 2019.
English Translation of Decision of refusal for Japanese Application No. 2020-542291, issued Sep. 26, 2023 (3 Pages).
English Translation of Office Action for Chinese Application No. 2201980010939.7, issued Sep. 1, 2023 (12 Pages).
Sandin, L.C. et al., "Local CTLA4 blockade effectively restrains experimental pancreatic adenocarcinoma growth in vivo," OncoImmunology, 3:1 (2014).
Schrörs et al., "MC38 colorectal tumor cell lines from two different sources display substantial differences in transcriptome, mutanome and neoantigen expression," Front. Immunol., 14:1102282, pp. 1-10 (2023).
Shields, N.J., et al., "Late-stage MC38 tumours recapitulate features of human colorectal cancer—implications for appropriate timepoint selection in preclinical studies," Front. Immunol., 14:1152035, pp. 1-23 (2023).
Wada, S., et al., "Sequencing CTLA-4 blockade with cell-based immunotherapy for prostate cancer," J Transl Med 11, 89 (2013).
Zamarin, et al., "Randomized Phase II Trial of Nivolumab Versus Nivolumab and Ipilimumab for Recurrent or Persistent Ovarian Cancer: an NRG Oncology Study," Clin Oncol, vol. 38, pp. 1814-1823 (2020).

* cited by examiner

*Primary Examiner* — Christina M Borgeest
(74) *Attorney, Agent, or Firm* — POLSINELLI PC

(57) ABSTRACT

This invention relates to anti-CTLA-4 antibody compositions that bind to the human CTLA-4 molecule, and the use of the compositions in cancer immunotherapy and for reducing autoimmune side effects compared to other immunotherapeutic agents.

6 Claims, 10 Drawing Sheets
Specification includes a Sequence Listing.

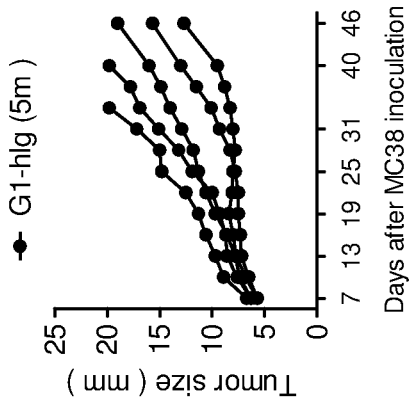
FIG. 8A
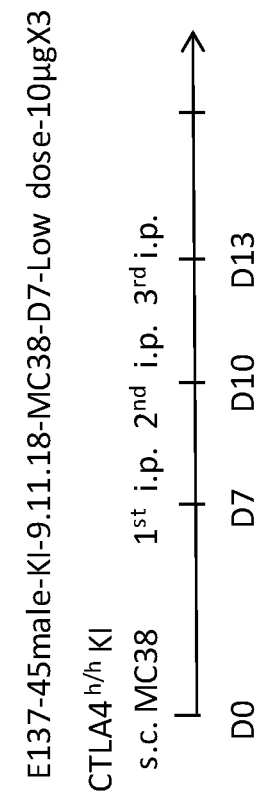
FIG. 8B
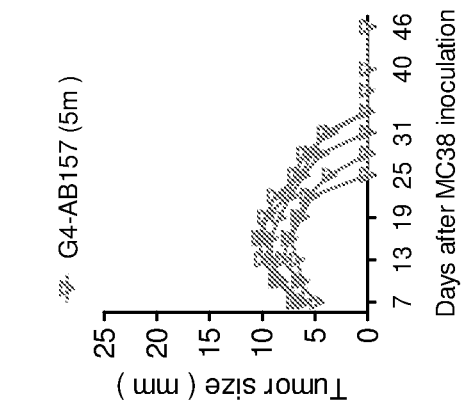
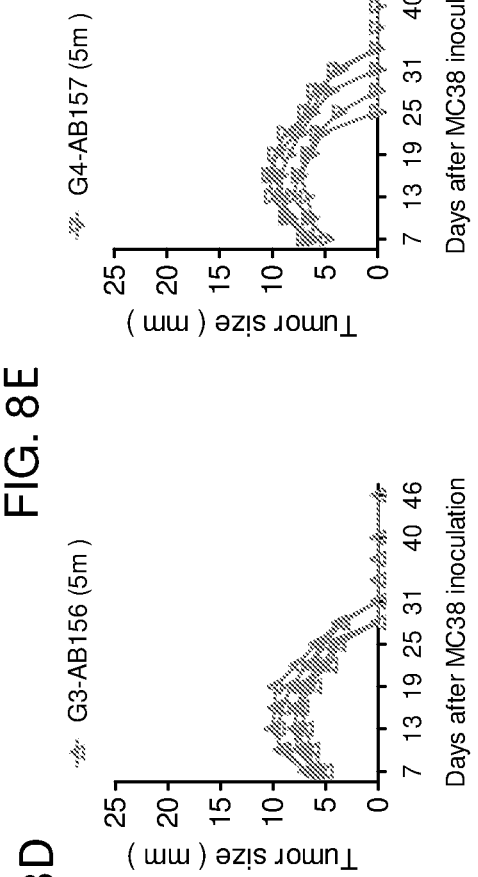
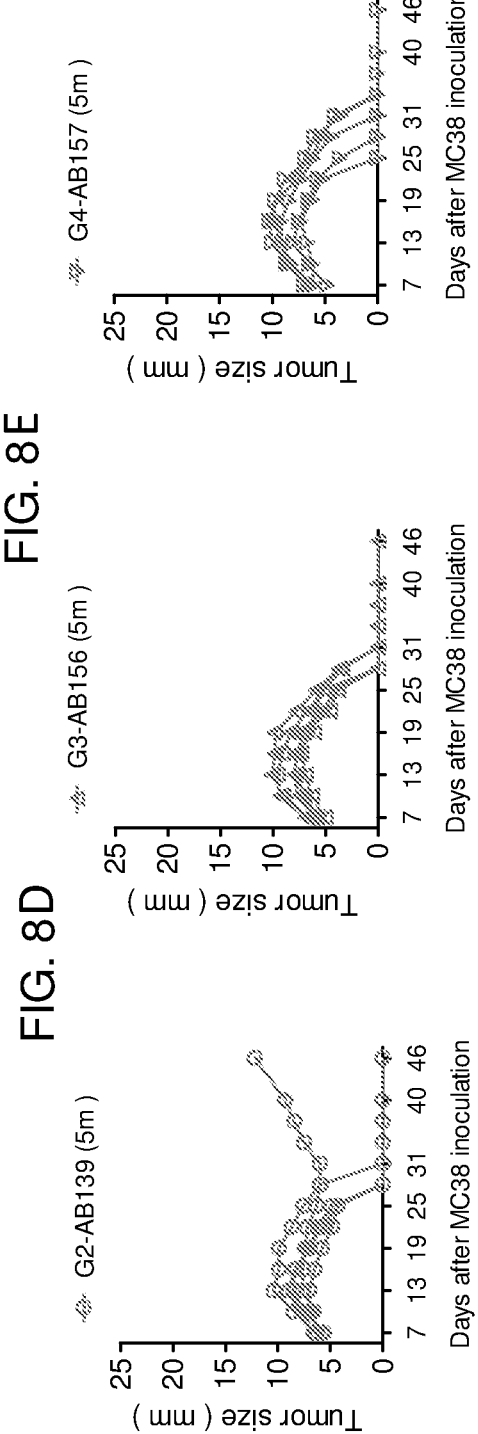
FIG. 8C
FIG. 8D
FIG. 8E

MUTANT ANTI-CTLA-4 ANTIBODIES WITH IMPROVED IMMUNOTHERAPEUTIC EFFECT BUT ATTENUATED ADVERSE EFFECTS

FIELD OF THE INVENTION

This invention relates to mutant anti-CTLA-4 antibodies with improved anti-tumor activities but attenuated adverse effects, and methods of making and using such antibodies.

BACKGROUND OF THE INVENTION

Anti-CTLA-4 monoclonal antibodies (mAbs) confer cancer immunotherapeutic effects (CITE), but cause severe immunotherapy-related adverse events (irAE). Anti-CTLA-4 mAbs have shown CITE in mouse models and melanoma patients. A combination of the anti-PD-1 mAb Nivolumab and anti-CTLA-4 mAb Ipilimumab significantly increased objective response rates of advanced melanoma patients. Promising results also emerged from this combination therapy in advanced non-small cell lung carcinoma (NSCLC). Tentative evidence of clinical benefits was obtained when another anti-CTLA-4 mAb (Tremelimumab) was combined with Durvalumab, an anti-PD-L1 mAb in a phase II clinical trial.

A major obstacle to broader clinical use of anti-CTLA-4 mAbs, either alone or in combination, is severe adverse events (SAEs). The SAEs observed in the Ipilimumab (the first clinical anti-CTLA-4 mAb) trials led to the concept of immunotherapy-related adverse events (irAE). In particular, in combination therapy with Ipilimumab and Nivolumab (anti-PD-1), more than 50% patients developed grade 3 and grade 4 SAE. In NSCLC, Ipilimumab and Nivolumab combination therapy resulted in high response rates, although the grade 3 and 4 SAEs also occurred at high rates. Likewise, the combination of Durvalumab (anti-PD-L1) and Tremelimumab (anti-CTLA-4 mAb) demonstrated clinical activity in NSCLC, although grade 3 and 4 SAEs and patient drop-off rate were high, presumably due to unacceptable toxicity. Since a higher dose of anti-CTLA-4 mAb is associated with better clinical outcomes in both monotherapy and combination therapy, irAE not only prevents many patients from continuing on immunotherapy, but also limits the efficacy of CITE. Furthermore, high numbers of patients drop off with both anti-CTLA-4 mAbs, which is likely attributed to the failure to meet clinical endpoints in several clinical trials.

More recently, a head-to-head comparison of anti-PD-1 mAb Nivolumab and anti-CTLA-4 mAb Ipilimumab as adjuvant therapy for resected stage III and IV melanoma showed that Ipilimumab had lower CITE but higher irAE, further dimming the prospect of CTLA-4-targeting immunotherapy. However, Ipilimumab-treated patients who survived for three years showed no further decline in survival rate over a ten-year period. The remarkably sustained response highlights the exceptional benefit of targeting this molecule for immunotherapy, especially if irAE can be brought under control.

A fundamental question for the generation of safe and effective anti-CTLA-4 mAbs is whether CITE and irAE are intrinsically linked. The classical checkpoint blockade hypothesis stipulates that anti-CTLA-4 mAbs promote cancer immunity by blocking a negative signal of B7-CTLA-4 interactions to promote naïve T cell activation in the lymphoid organ. According to this model, therapeutic antibodies are antagonists that functionally inactivate CTLA-4-B7 interactions. Since genetic inactivation of CTLA-4 expression leads to autoimmune diseases in mouse and human, it is assumed that the irAE would be a necessary price for CITE. On the other hand, we demonstrated that rather than blocking B7-CTLA-4 interactions, the therapeutic effect of anti-mouse CTLA-4 mAbs requires antibody-mediated depletion of Treg specifically within tumor microenvironment. It is not relevant whether an antibody is capable of blocking B7-CTLA-4 interactions under physiological conditions for the induction of CITE. These studies raise the intriguing possibility that CITE can be achieved without irAE if one can achieve local Treg depletion without mimicking the genetic inactivation of CTLA-4 expression. Using mice that were either homozygous or heterozygous for a human allele, it was found that irAE required biallelic engagement, while CITE only required monoallelic engagement. These data suggest that irAE requires antagonizing CTLA-4 function; while CITE depends on an agonist activity of the antibodies.

SUMMARY OF THE INVENTION

Provided herein are methods of abrogating the antagonist activity of anti-CTLA-4 antibodies while preserving and improving on their Fc receptor agonist activity. Specifically disclosed are methods of increasing the sensitivity of antibody binding to acidic pH whereby the anti-CTLA-4 antibody demonstrates reduced binding to CTLA-4. A change, such as a reduction in an anti-CTLA-4 antibody binding activity, as described herein, may be the relative difference between two different pH levels for a particular antibody composition. In one embodiment, binding to CTLA-4 is reduced at a pH that reflects the intracellular endosomal compartment. In a preferred embodiment, binding to CTLA-4 is reduced at an endosomal pH of 5.5 by more than 50% relative to binding at neutral pH (pH 7.0). Such a reduction may reach more than 75% at lysosomal pH 4.5 as compared to pH 7.0. The antibody-antigen complex preformed at pH 7.0 may dissociate under an acidic environment of pH 4.5-6.0. The reduction in binding may also be in comparison to a reference antibody which may be considerably less pH sensitive using the same standard. The reference antibody may be an antibody known in the art such as Ipilimumab or Tremelimumab. In the context of an engineered antibody, the changes may also be in comparison to a wild-type antibody which may be considerably less pH sensitive using the same standard.

In another aspect, provided herein are methods of identifying anti-CTLA-4 antibodies with improved anti-tumor efficacy and/or reduced toxicity, comprising testing or measuring the interaction between plate-coated CTLA-4 and soluble antibodies, at one more pHs in a range of 4.5 to 7.0, and selecting antibodies with increased pH sensitivity such that reduced binding is observed at acidic pH. In one embodiment, the pHs are 7.0 and 5.5. In other, they are 7.0 and 4.5, or 7.0, 5.5 and 4.5.

In another aspect, provided herein are methods of identifying anti-CTLA-4 antibodies with reduced toxicity by their effect on levels of cell surface CTLA-4. In a preferred embodiment the antibody may dissociate from CTLA-4 within a cell and allow CTLA-4 to recycle back to the cell surface, which can be determined based on minimal or no reduction in cell surface CTLA-4.

In another aspect, provided herein are methods of designing or modifying anti-CTLA-4 antibodies to improve the anti-tumor effect and/or reduce toxicity by increasing pH sensitivity, such that reduced binding to CTLA-4 is observed at acidic pH. Also provided are anti-CTLA-4 antibodies that exhibit these characteristics. In one embodiment, the antibodies may be designed by replacing one or more tyrosine residues within or near one or more CDR regions of the light and/or heavy chain variable regions of a wild-type anti-CTLA-4 antibody, such as Ipilimumab or Tremelimumab, with histidine residues. Mutant versions of the anti-CTLA-4 antibody, Tremelimumab or Ipilimumab, may be generated so that they have reduced binding to CTLA-4 at acidic pH relative to the wild-type antibodies.

In another aspect, provided herein are methods of identifying antibodies with improved anti-tumor efficacy using an ADCC reporter assay, wherein enhanced ADCC activity is used as a readout for anti-tumor activity.

Also provided herein are specific anti-CTLA-4 antibodies, antibody fragments thereof and compositions of the foregoing, with enhanced anti-tumor activity and/or reduced toxicity. The antibody may comprise a heavy chain comprising the sequence set forth in SEQ ID NO: 1, 3, 5, 6 or 8, and a light chain comprising the sequence set forth in SEQ ID NO: 2 or 4. The antibody may also comprise a heavy chain comprising the sequence set forth in one of SEQ ID NOS: 14-18, and a light chain comprising the sequence set forth in one of SEQ ID NOs: 10-12.

Further provided herein are methods of cancer immunotherapy or treating cancer, whereby an anti-CTLA-4 antibody composition described herein is used alone or in combination with one or more other anti-cancer therapies. In one aspect the other anti-cancer therapy is an immunotherapy. In another aspect the immunotherapy is an anti-PD-1 or anti-PD-L1 therapy. The immunotherapy may be Nivolumab, Durvalumab or Pembrolizmab. Also provided are uses of an antibody composition described herein in the manufacture of a medicament for treating cancer. The method of treating cancer may comprise administering a composition described herein to a subject in need of cancer treatment. The subject may be a human.

BRIEF DESCRIPTION OF THE DRAWINGS

FIG. 4. pH sensitivity of antibodies dissociated from CTLA-4 in live cells after endocytosis. 293T stable cell lines expressing hCTLA-4 were labeled with anti-CTLA-4 mAbs at 4° C. for 30 min and, after washing out of the unbound antibodies, cells were transferred to 37° C. for 1 h. Antibody-bound surface CTLA-4 was captured by protein-G beads and detected by western blot using anti-CTLA-4 Antibody (H-126): sc-9094 (Santa Cruz biotechnology).

FIG. 8A-E. Immunotherapeutic effect of TremeIgG1 and its pH-sensitive variants. FIG. 8A. Diagram of the experimental design. FIGS. 8B-E. Tumor growth in mice receiving either IgG-Fc (FIG. 8B), TremeIgG1 (AB139; FIG. 8C), AB156 (FIG. 8D) or AB157 (FIG. 8E).

DETAILED DESCRIPTION

Definitions

Figure 1:
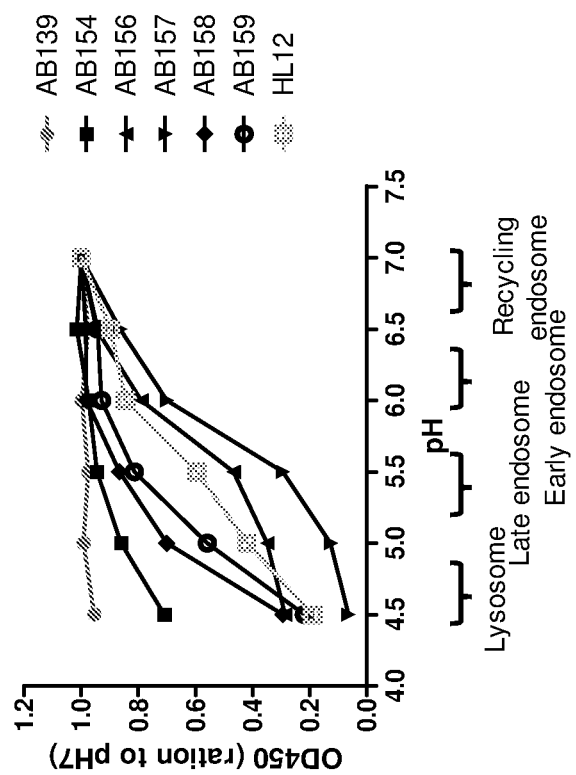
FIG. 1A-B. pH-sensitivity of TremeIgG1 and its variants. His-hCTLA-4 (0.5 µg/ml) was coated in ELISA plates and different anti-CTLA-4 mAbs were added at 1 µg/ml in the buffer over a pH range of 4.5 to 7.0. pH indicated represents binding and washing conditions. Antibodies bound to CTLA-4 were measured using horse-radish perioxidase-labeled anti-human IgG antibodies.
Figure 1:
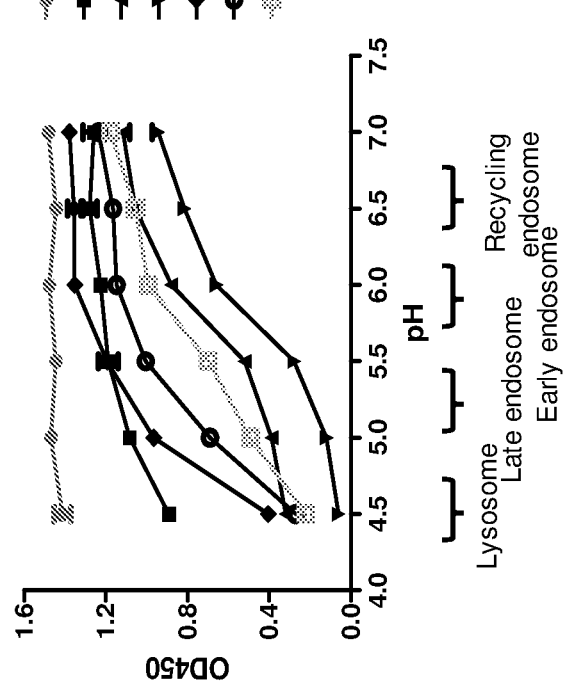

As used herein, the term "antibody" refers to an immunoglobulin molecule that possesses a "variable region" antigen recognition site. The term "variable region" refers to a domain of the immunoglobulin that is distinct from a domains broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; ref. 44) and may comprise those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain). "Framework Region" or "FR" residues are those variable domain residues other than the hypervariable region residues as herein defined. An antibody disclosed herein may be a monoclonal antibody, multi-specific antibody, human antibody, humanized antibody, synthetic antibody, chimeric antibody, camelized antibody, single chain antibody, disulfide-linked Fv (sdFv), intrabody, or an anti-idiotypic (anti-Id) antibody (including, e.g., anti-Id and anti-anti-Id antibodies to antibodies of the invention). In particular, the antibody may be an immunoglobulin molecule, such as IgG, IgE, IgM, IgD, IgA or IgY, or be of a class, such as IgG$_1$, IgG$_2$, IgG$_3$, IgG$_4$, IgA$_1$ or IgA$_2$, or of a subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site, and exhibit an ability to immunospecifically bind antigen. Such fragments include Fab', F(ab')$_2$, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, chimeric or humanized antibodies are particularly preferred for in vivo use in humans, however, murine antibodies or antibodies of other species may be advantageously employed for many uses (for example, in vitro or in situ detection assays, acute in vivo use, etc.).

A "chimeric antibody" is a molecule in which different portions of the antibody are derived from different immunoglobulin molecules such as antibodies having a variable region derived from a non-human antibody and a human immunoglobulin constant region. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; 46-48), and chain shuffling (U.S. Pat. No. 5,565,332), the contents of all of which are incorporated herein by reference.

Antibodies described herein may be humanized antibodies. As used herein, the term "humanized antibody" refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. The donor antibody is referred to as being "humanized," by the process of "humanization," because the resultant humanized antibody is expected to bind to the same antigen as the donor antibody that provides the CDRs. Humanized antibodies may be human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications may further refine antibody performance. The humanized antibody may comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody may optionally also comprise at least a portion of an immunoglobulin constant region (Fc), which may be that of a human immunoglobulin that immunospecifically binds to an FcγRIIB polypeptide, that has been altered by the introduction of one or more amino acid residue substitutions, deletions or additions (i.e., mutations).

1. Anti-CTLA-4 Antibody Compositions

Antibodies against human CTLA-4 protein, including Ipilimumab and Tremelimumab, have been shown to increase survival of cancer patients, either as the only immunotherapeutic agent or in combination with another therapeutic agent such as an anti-PD-1 antibody. However, the therapeutic effect is associated with significant adverse effects. There is a great need to develop novel anti-CTLA-4 antibodies to achieve better therapeutic effects or fewer autoimmune adverse effects. The inventors have discovered anti-CTLA-4 antibodies that, surprisingly, can be used to induce cancer rejection while also reducing autoimmune adverse effects associated with immunotherapy.

Provided herein are antibodies and antigen-binding fragments thereof, and compositions comprising the foregoing. The composition may be a pharmaceutical composition. The antibody may be an anti-CTLA-4 antibody. The antibody may be a monoclonal antibody, a human antibody, a chimeric antibody or a humanized antibody. The antibody may also be monospecific, bispecific, trispecific, or multispecific.

The antibody may be detectably labeled, and may comprise a conjugated toxin, drug, receptor, enzyme, or receptor ligand.

Also provided herein is an antigen-binding fragment of an antibody that immunospecifically binds to CTLA-4, and in particular human CTLA-4, which may be expressed on the surface of a live cell at an endogenous or transfected concentration. The antigen-binding fragment may bind to CTLA-4, and the live cell may be a T cell.

In a particular embodiment, the anti-CTLA-4 antibody may efficiently induce Treg depletion and Fc receptor-dependent tumor rejection. In another embodiment, the anti-CTLA-4 antibody may dissociate from CTLA-4 under intracellular acidic pH indications, allowing CTLA-4 to recycle back to the cell surface.

Further provided herein are the design of novel anti-CTLA-4 antibodies, and ways to improve the efficacy or toxicity profile of existing anti-CTLA-4 antibodies, by incorporating the functional characteristics or attributes of the antibodies described herein.

The antibody may comprise a mutant form of an amino acid sequence of a known anti-CTLA-4 antibody, which may be Ipilimumab or Tremelimumab. In comparison to the wild-type antibody sequence, the mutant sequence may comprise one or more substitutions of tyrosine with histidine near or within one or more CDR1, CDR2, and CDR3 regions of at least one heavy or light chain. The anti-CTLA-4 antibody may comprise a heavy chain comprising the sequence set forth in one of SEQ ID NOs: 1, 3, 5, 6 and 8, and a light chain comprising the sequence set forth in one of SEQ ID NOs: 2 and 4. In particular, the heavy chain may comprise the sequence set forth in SEQ ID NO: 6 and the light chain may comprise the sequence set forth in SEQ ID NO: 2. The heavy chain may also comprise the sequence set forth in one of SEQ ID NOs: 14-18 and the light chain may comprise the sequence set forth in one of SEQ ID NOs: 10-12.

2. Methods of Improving the Efficacy and Safety of Anti-CTLA-4 Antibody Compositions Provided herein are methods of designing (mutating or engineering) or selecting antibody compositions that exhibit improved anti-tumor activity and/or safety. Specifically, the sensitivity of antibody binding at acidic pH may be increased, whereby the anti-CTLA-4 antibody demonstrates reduced binding to CTLA-4 at lower pH. In one embodiment, binding to CTLA-4 is reduced at a pH that reflects the endosomal compartment. In a preferred embodiment, binding to CTLA-4 is reduced at pH 5.5 relative to binding at neutral pH (pH 7.0). Such reduced binding at pH 5.5 may be 50% or more of the CTLA-4 binding observed at neutral pH. A change, such as a reduction or increase, in an anti-CTLA-4 antibody activity described herein, such as binding, may be in comparison to a reference or wild-type antibody. The reference antibody may be an antibody known in the art such as Ipilimumab or Tremelimumab. The change may also be relative between two different pH levels of a particular antibody composition described herein.

Anti-CTLA-4 antibodies may be identified with improved anti-tumor efficacy and/or reduced toxicity by testing the interaction between plate-coated CTLA-4 and soluble antibodies over a pH range of 4.5 to 7.0, and selecting antibodies with increased pH sensitivity such that reduced binding is observed at acidic pH.

Anti-CTLA-4 antibodies may be identified with reduced toxicity by their effect on the levels of cell surface CTLA-4. In a preferred embodiment the antibody dissociates from CTLA-4 within the cell and allow CTLA-4 to recycle back to the cell surface, which can be determined based on minimal or no reduction in cell surface CTLA-4, or a reduction in the amount of antibody-bound surface CTLA-4.

Provided herein are methods of designing or modifying anti-CTLA-4 antibodies to improve the anti-tumor effect and/or reduce toxicity by increasing pH sensitivity such that reduced binding to CTLA-4 is observed at acidic pH. In one embodiment, the antibodies are designed by replacing one or more tyrosine residues within or near the CDR regions of the light and/or heavy chain variable regions of the antibody with histidine residues. The method may comprise generating mutant versions of the anti-CTLA-4 antibody Tremelimumab or Ipilimumab that display reduced binding to CTLA-4 at acidic pH.

Antibodies may be designed or modified for improved anti-tumor efficacy using an ADCC reporter assay, wherein enhanced ADCC activity is used as a readout for anti-tumor activity. In a preferred embodiment, to increase the anti-tumor activity, CTLA-4 targeting agents will selectively deplete Tregs in the tumor microenvironment. In a particular embodiment, the anti-CTLA-4 mAbs have increased Fc mediated Treg depleting activity. Treg depletion can occur by Fc mediated effector function such as antibody-dependent cell-mediated cytotoxicity (ADCC) or antibody-dependent cell-mediated phagocytosis (ADCP). The Fc mediated effector function can be introduced or enhanced by any method known in the art. In one example the antibody is as IgG1 isotype, which has increased effector function compared to other isotypes. The Fc mediated effector function can be further enhanced by mutation of the amino acid sequence of the Fc domain. For example, three mutations (S298A, E333A and K334A) can be introduced into the CH region of the Fc domain to increase ADCC activity. Antibodies used for ADCC mediated activity usually require some kind of modification in order to enhance their ADCC activity. There are a number of technologies available for this which typically involves engineering the antibody so that the oligosaccharides in the Fc region of the antibody do not have any fucose sugar units, which improves binding to the FcγIIIa receptor. When antibodies are afucosylated the effect is to increase antibody-dependent cellular cytotoxicity (ADCC). For example, Biowa's POTELLIGENT® technology uses a FUT8 gene knockout CHO cell line to produce 100% afucosylated antibodies. FUT8 is the only gene coding a1,6-Fucosyltransferase which catalyzes the transfer of Fucose from GDP-Fucose to GlcNAc in a1,6-linkage of complex-type oligosaccharide. Probiogen has developed a CHO line that is engineered to produce lower levels of fucosylated glycans on MAbs, although not through FUT knockout. Probiogen's system introduces a bacterial enzyme that redirects the de-novo fucose synthesis pathway towards a sugar-nucleotide that cannot be metabolized by the cell. As an alternative approach, Seattle Genetics has a proprietary feed system which will produce lower levels of fucosylated glycans on MAbs produced in CHO (and perhaps other) cell lines. Xencor has developed an XmAb Fc domain technology is designed to improve the immune system's elimination of tumor and other pathologic cells. This Fc domain has two amino acid changes, resulting in a 40-fold greater affinity for FcγRIIIa. It also increases affinity for FcγRIIa, with potential for recruitment of other effector cells such as macrophages, which play a role in immunity by engulfing and digesting foreign material.

3. Methods of Treatment

The antibody compositions described herein, or antibodies designed based on the methods described herein, may be used to upregulate immune responses. Up-modulation of the immune system is particularly desirable in the treatment of cancers and chronic infections, and thus the antibody compositions described herein have utility in the treatment of such disorders. As used herein, the term "cancer" refers to a neoplasm or tumor resulting from abnormal uncontrolled growth of cells. "Cancer" explicitly includes leukemias and lymphomas. The term "cancer" also refers to a disease involving cells that have the potential to metastasize to distal sites.

An antibody composition described herein may be used in the manufacture of a medicament. The composition may also be administered to a subject in need of treatment. The subject may be a human. The subject may be in need of treatment of a disease or condition described herein.

Accordingly, the methods and compositions described herein may be useful in the treatment or prevention of one or more of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

The antibody compositions and antigen binding fragments thereof may be used with another anti-tumor therapy, which may be selected from but not limited to, current standard and experimental chemotherapies, hormonal therapies, biological therapies, immunotherapies, radiation therapies, and surgery. In some embodiments, a composition described herein may be administered in combination with a therapeutically or prophylactically effective amount of one or more agents, therapeutic antibodies or other agents known to those skilled in the art for the treatment or prevention of cancer, autoimmune disease, infectious disease or intoxication. Such agents include for example, any of the above-discussed biological response modifiers, cytotoxins, antimetabolites, alkylating agents, antibiotics, anti-mitotic agents, or immunotherapeutics.

The antibody compositions and antigen binding fragments thereof may be used with another anti-tumor immunotherapy. In such an embodiment, the composition is administered in combination with a molecule that disrupts or enhances alternative immunomodulatory pathways (such as TIM3, TIM4, OX40, CD40, GITR, 4-1-BB, B7-H1, PD-1, B7-H3, B7-H4, LIGHT, BTLA, ICOS, CD27 or LAG3) or modulates the activity of effecter molecules such as cytokines (e.g., IL-4, IL-7, IL-10, IL-12, IL-15, IL-17, GF-beta, IFNg, Flt3, BLys) and chemokines (e.g., CCL21) in order to enhance the immunomodulatory effects. Specific embodiments include a bi-specific antibody comprising an anti-CTLA-4 antibody described herein or antigen binding fragment thereof, in combination with anti-PD-1 (pembrolizumab (Keytruda) or Nivolumab (Opdivo)), anti-B7-H1 (atezolizumab (Tecentriq) or durvalumab (Imfinzi)), anti-B7-H3, anti-B7-H4, anti-LIGHT, anti-LAG3, anti-TIM3, anti-TIM4 anti-CD40, anti-OX40, anti-GITR, anti-BTLA, anti-CD27, anti-ICOS or anti-4-1BB. In yet another embodiment, an antibody of the invention or antigen binding fragment thereof is administered in combination with a molecule that activates different stages or aspects of the immune response in order to achieve a broader immune response, such as IDO inhibitors. In more preferred embodiment, the antibody compositions and antigen binding fragments thereof are combined with anti-PD-1 or anti-4-1BB antibodies, without exacerbating autoimmune side effects.

The composition described herein may comprise a bi-specific antibody that comprises an anti-CTLA-4 antibody bridged to an antibody that binds another immune stimulating molecule. Specific embodiments include a bi-specific antibody comprising the anti-CTLA-4 antibody compositions described herein and anti-PD-1, anti-B7-H1, anti-B7-H3, anti-B7-H4, anti-LIGHT, anti-LAG3, anti-TIM3, anti-TIM4 anti-CD40, anti-OX40, anti-GITR, anti-BTLA, anti-CD27, anti-ICOS or anti-4-1BB. Such antibodies may be used as a medicament, and may be used to treat cancer.

4. Production

The anti-CTLA-4 antibodies described herein and antigen binding fragments thereof may be prepared using a eukaryotic expression system. The expression system may entail expression from a vector in mammalian cells, such as Chinese Hamster Ovary (CHO) cells. The antibodies may also be produced from a stable cell line that expresses the antibody from a vector or a portion of a vector that has been integrated into the cellular genome.

The anti-CTLA-4 antibodies described herein and antigen binding fragments thereof can be purified using, for example, chromatographic methods such as affinity chromatography, ion exhange chromatography, hydrophobic interaction chromatography, DEAE ion exchange, gel filtration, and hydroxylapatite chromatography. In some embodiments, fusion proteins can be engineered to contain an additional domain containing an amino acid sequence that allows the polypeptides to be captured onto an affinity matrix. For example, the antibodies described herein comprising the Fc region of an immunoglobulin domain can be isolated from cell culture supernatant or a cytoplasmic extract using a protein A or protein G column. In addition, a tag such as c-myc, hemagglutinin, polyhistidine, or Flag™ (Kodak) can be used to aid antibody purification. Such tags can be inserted anywhere within the polypeptide sequence, including at either the carboxyl or amino terminus. Other fusions that can be useful include enzymes that aid in the detection of the polypeptide, such as alkaline phosphatase. Immunoaffinity chromatography also can be used to purify polypeptides.

5. Pharmaceutical Compositions

The invention further concerns a pharmaceutical composition comprising a therapeutically effective amount of any of the above-described anti-CTLA-4 antibody compositions or antigen binding fragments thereof, and a physiologically acceptable carrier or excipient. Preferably, compositions of the invention comprise a prophylactically or therapeutically effective amount of the anti-CTLA-4 antibody or its antigen binding fragment and a pharmaceutically acceptable carrier In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers may be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, trehalose, gelatin, malt, rice, flour, chalk, silica gel, sodium stearate, glycerol monostearate, talc, sodium chloride, dried skim milk, glycerol, propylene, glycol, water, ethanol and the like. The composition, if desired, may also contain minor amounts of wetting or emulsifying agents, such as Poloxamer or polysorbate, or pH buffering agents. These compositions may take the form of solutions, suspensions, emulsion, tablets, pills, capsules, powders, sustained-release formulations and the like.

Generally, the ingredients of compositions of the invention may be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline may be provided so that the ingredients may be mixed prior to administration.

The compositions of the invention may be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The anti-CTLA-4 antibody compositions described herein, or antigen binding fragments thereof, may also be formulated for lyophilization to allow long term storage, particularly at room temperature. Lyophilized formulations are particularly useful for subcutaneous administration.

6. Methods of Administration

Methods of administering the compositions described herein include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

EXAMPLES

Example 1

Generation of Tremelimumab Variants that Lose Binding Activity at Low pH

Since genetic inactivation of CTLA-4 results in severe auto-inflammatory lymphoproliferative diseases, the inventors realized that antibodies that antagonize or cause degradation of CTLA-4 would be irAE prone. Given the fact that many antigen-antibody complexes can travel to lysosomes and get degraded, the inventors realized that antibodies that lost binding to CTLA-4 before the complex reached lysosomes would dissociate and allow recycling of the antigen and/or antibody molecules. Since the lysosomal compartment can have a pH of <5.0, variants of Tremelimumab and Ipilimumab that would lose binding to CTLA-4 molecules at low pH were generated through site-directed mutagenesis of the VL and VH CDR regions. As histidine has a side chain with a pK of 5.97, antibodies incorporating histidine residues are likely to have a charge change at around pH 5.5-6.0. To have maximal impact, mutations were made in the CDR regions of both Tremelimumab and Ipilimumab.

Eight antibodies comprising the light chain and heavy of either WT or mutant Tremelimumab variable regions were generated. Because Treg-depleting activity is important for tumor rejection, the human IgG2 constant region in Tremelimumab was replaced with that of IgG1, and the product is thereby referred as TremeIgG1 (AB139) and the mutant antibodies are referred to as TremeIgG1M (AB154-159). The composition and affinity of the antibodies are listed in Table 1.

TABLE 1

Tremelimumab variants: composition and affinities.

| Antibody | Heavy Chain | Light Chain | $K_{D\,(M)}$ |
|---|---|---|---|
| AB139 (TremeIgG1) | SEQ ID NO: 1 | SEQ ID NO: 2 | 1.466E−10 |
| AB154 | SEQ ID NO: 3 | SEQ ID NO: 2 | 1.228E−09 |
| AB155 | SEQ ID NO: 3 | SEQ ID NO: 4 | no binding |
| AB156 | SEQ ID NO: 5 | SEQ ID NO: 2 | 4.459E−09 |
| AB157 | SEQ ID NO: 6 | SEQ ID NO: 2 | 2.322E−09 |
| AB158 | SEQ ID NO: 7 | SEQ ID NO: 2 | 5.425E−10 |
| AB159 | SEQ ID NO: 8 | SEQ ID NO: 2 | 3.867E−10 |

Using a similar approach mutants of the Ipilimumab parental heavy (SEQ ID NO: 13) and light (SEQ ID NO: 9) chains were generated. This resulted in the heavy chain mutants having SEQ ID NOS: 14-18 and the light chain mutants having SEQ ID NOS: 9-12. The sequences listed in SEQ ID NOS. 1-18 are examples, and additional mutations in the CDR regions or near the antigen binding sites of the antibodies can be made based the same principle.

In order to validate the approach, the activity of the Tremelimumab mutant antibodies was evaluated. To determine if the introduction of histidine to the CDR regions affects the pH sensitivity of the antibodies, the antibody binding to its antigen, polyhistidine-tagged CTLA-4, was measured over a pH range. The raw data are presented in FIG. 1A, while the normalized binding are shown in FIG. 1B. As a control, HL12, which is known to bind CTLA-4 in a pH-dependent manner, with reduced binding at low/acidic pH, was used. These data demonstrated that while TremeIgG1 binds to CTLA-4 at all pH tested, all mutants showed varying degrees of pH sensitivity at acidic pH. Among them, Ab154, Ab158, and Ab159 were less sensitive than HL12, while Ab156 and Ab157 exhibited higher pH sensitivity. Importantly, at the pH found in late endosomes (pH5.5), HL12, Ab156 and Ab157 showed 50% or less binding relative to neutral pH (pH 7.0), while that of Ab158 and Ab159 still exhibit 75% or more binding compared to neutral pH. Moreover, the pH-dependence is not due to low antibody affinity at neutral pH, given that when compared with Ab158, Ab159 showed somewhat higher pH sensitivity despite higher affinity. Likewise, Ab157 exhibit higher affinity and higher pH-sensitivity, Ab155 did not bind to CTLA-4 and was excluded from this analysis.

Figure 2:
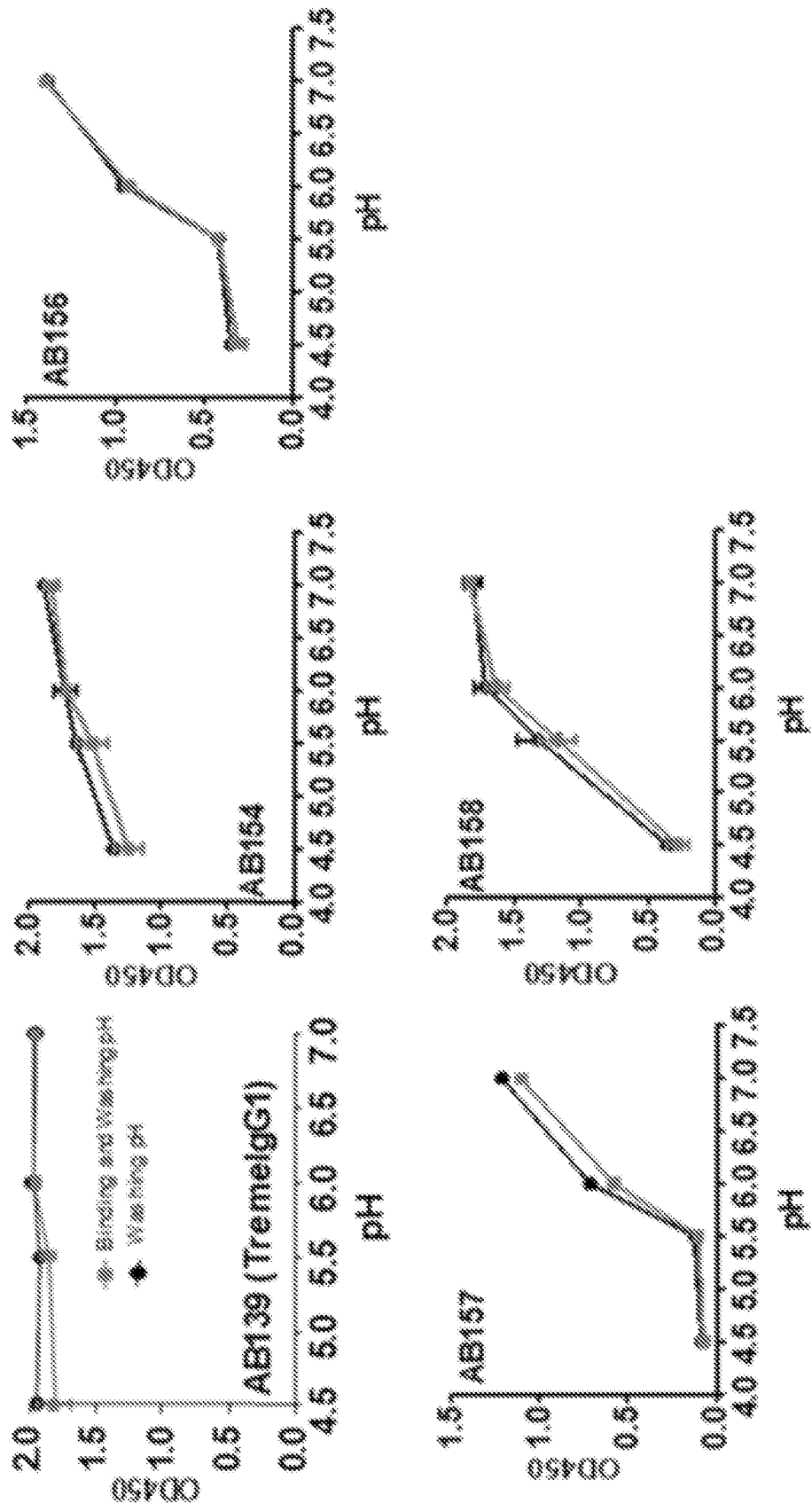
FIG. 2. pH-sensitive binding dissociation of TremeIgG1 and its variants. As in FIG. 1, except that a group in which the antibodies were bound to plate-bound CTLA-4 at pH 7.0, and then the plates were washed with buffers of indicated pH.
Figure 3:
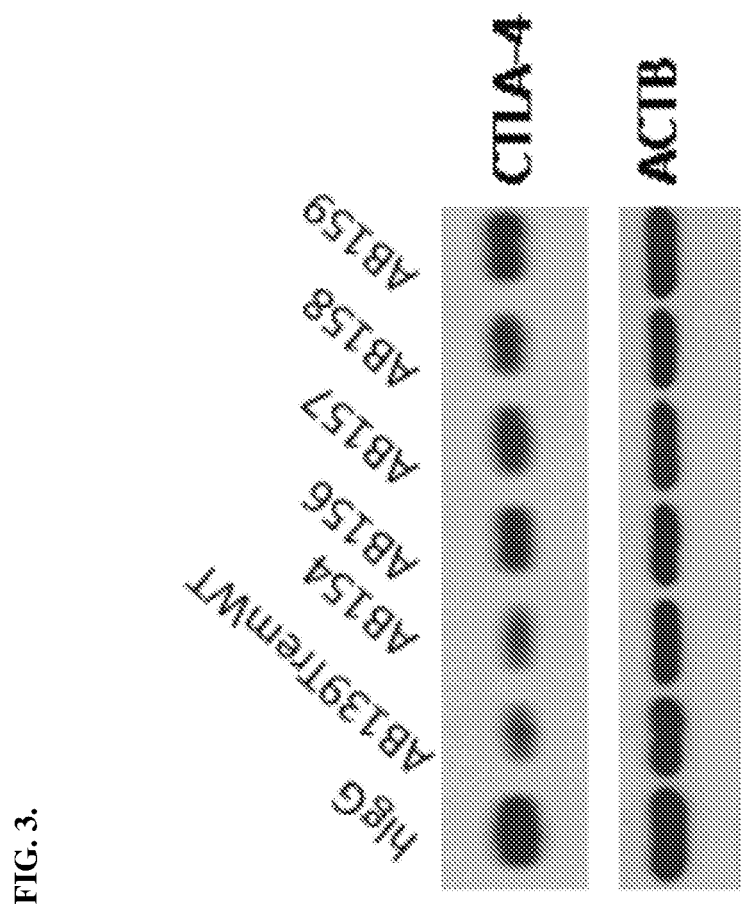
FIG. 3. The effect of anti-CTLA-4 antibodies on total CTLA-4 levels. CHO cells transfected with human CTLA-4 cDNA were incubated with anti-CTLA-4 antibodies for 4 hours at 37° C. and the total amount of CTLA-4 in the cells was determined by Western blot of total cell lysates. CTLA-4 down-regulation is induced by TremeIgG1 and mAb154 but much less so by other antibody variants.
Figure 4B:
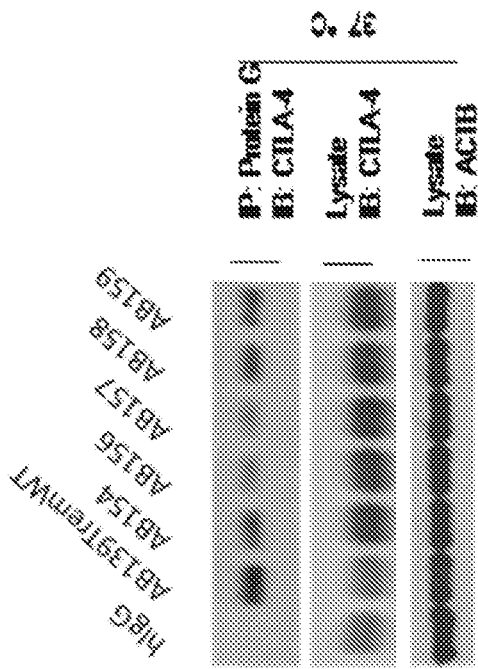
FIG. 4B shows the level of antibody remaining after incubation at 37° C. Engineered antibodies, especially AB156 and AB157, dissociate from CTLA-4 during antibody-induced Internalization at 37° C. compared with mAb139 (TremeIgG1) or other variants with less pH sensitivity.
Figure 4A:
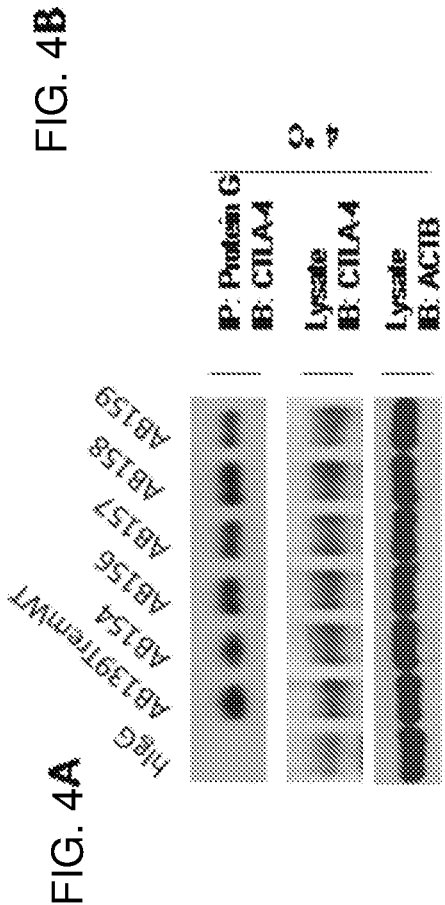
FIG. 4A shows binding of the antibodies at 4° C.
Figure 5:
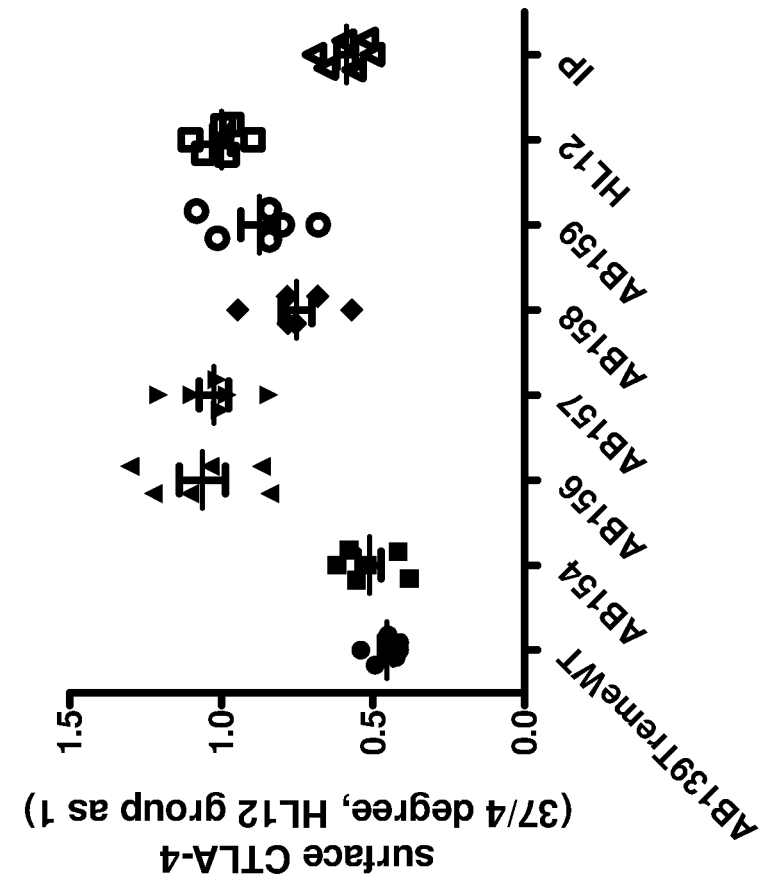
FIG. 5. Effect of anti-CTLA-4 antibodies on cell surface CTLA-4. Human CTLA-4-expressing CHO cells were treated with TremeIgG1 and its mutants for 2 hours at 37° C. or 4° C. After washing out the unbound antibodies, surface CTLA-4 was detected by anti-hIgG (H+L)-alex488 for half an hour at 4° C. and analyzed by flow cytometry. The data presented are the ratio of MFI for samples incubated at 37° C. over that at 4° C., and have been normalized against the ratio of HL12, the means of which is defined as 1.0. Data shown are from three independent experiments, each include two samples per group.
Figure 6:
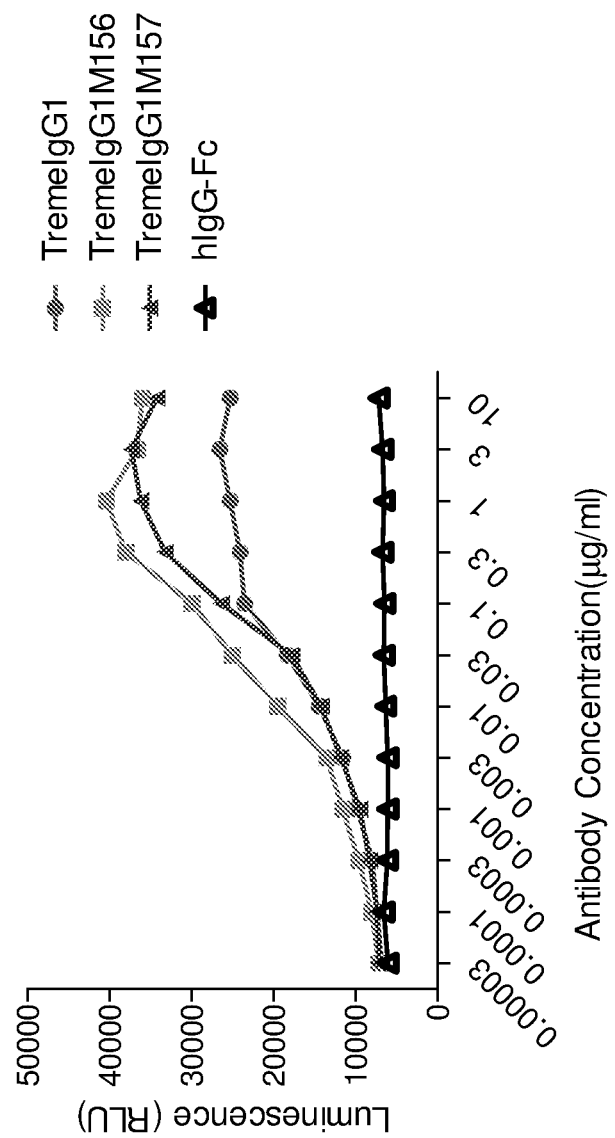
FIG. 6. ADCC activity of TremeIgG1 and its pH sensitive variants. Data shown are Luminescence units emitted from reporter cells expressing FcγRIIIA 293T cells expressing human CTLA-4 molecule are used as target cells.
Figure 7:
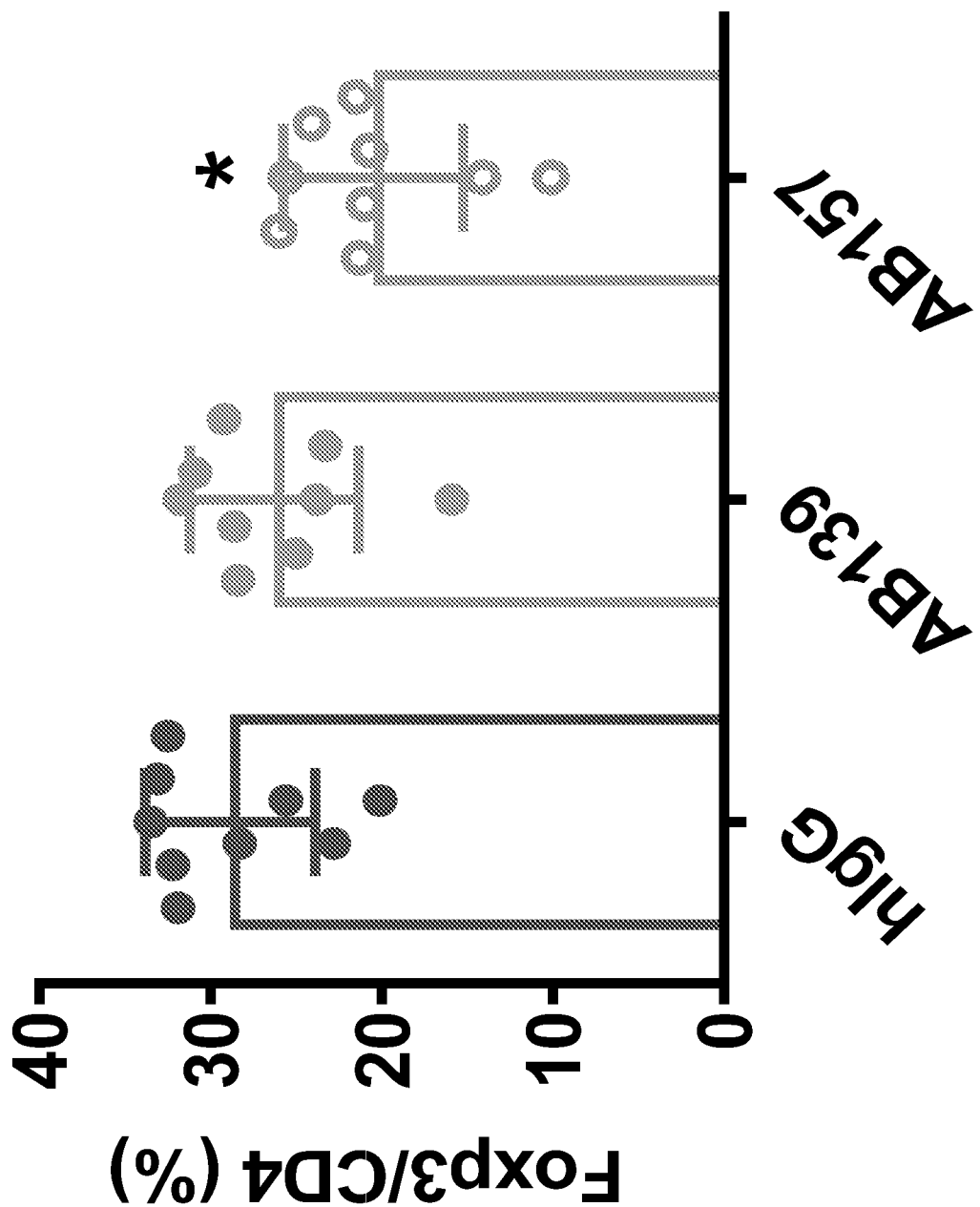
FIG. 7. Ab157 exhibits improved activity in the depletion of Tregs in the tumor microenvironment. MC38 bearing-Ctla4$^{h/h}$ mice (n=9) were i.p. treated with either TremeIgG1 (AB139) or its pH sensitivity variant Ab157 (30 µg/mouse) on day 14 after tumor inoculation. Selective depletion of Treg cells in the tumor microenvironment were determined by % Treg cells among CD4 T cells at 16 hours after antibody treatment. *P<0.05.

Since the anti-CTLA-4 antibodies bound to CTLA-4 under neutral pH under physiological condition, and since the antibody-antigen complex traffics through a progressively acidic environment, pH sensitivity and dissociation were measured at different pHs. As shown in FIG. 2, pH sensitive antibodies identified by binding and washing at acidic and neutral pH also dissociate from CTLA-4 at acidic pH with similar ranking.

To dissociate antibody from the antigen within the acidic pH of endosomes, tyrosine (Y) was replaced with histidine in the CDRs of TremeIgG1. Histidine was introduced at varying numbers of five continuous Y residues in CDR3 and two continuous Y residues in CDR2. Variants with two or three continuous Y to H mutations (Ab157 and Ab156) in CDR3 exhibit more pH sensitivity than the single Y to H mutation (Ab 158) or the two Y to H mutations in CDR2 (Ab159). Ab156 and 157 start to release CTLA-4 at early endosome pH 6, and showed 50% or less binding at pH found in late endosome (pH 5.5). While Ab158 and Ab159 still exhibit 75% or more binding at pH 5.5.

His mutations were also introduced at Ser31, Tyr32 and Trp36 in the heavy chain variable CDR1 (Ab 154), or combinational mutations at Tyr32 and Asp34 in the light chain CDR1 (Ab155). Although comparable mutations have been reported to be essential for pH dependent antigen binding for other antibodies, they have not resulted in desirable pH-sensitivity of TremeIgG1: Ab154 exhibited only minor loss of CTLA-4 binding under pH 5.5, while Ab 155 exhibit no measurable binding to CTLA-4 in neutral pH. The data suggest that replacing multiple tyrosines with histidines in the tyrosine rich regions of CDRs represents a simple way to obtain pH-sensitive antibodies while preserving its binding to antigen under neutral pH.

Example 2

Identification of Antibodies that do not Reduce Cell Surface CTLA-4 Levels

To determine the effect of anti-CTLA-4 antibodies on total CTLA-4 levels, the Tremelimumab antibodies were incubated with CHO cells transfected with human CTLA-4 cDNA for 4 hours at 37° C. The total amounts of CTLA-4 in the cells were determined by Western blot of the total cell lysates. As shown in FIG. 3, a significant reduction of CTLA-4 was induced by WT TremeIgG1 and its variant Ab154. Much less reduction was induced by the other mutant antibodies.

To determine if the pH sensitivity of antibodies causes their dissociation from CTLA-4 in live cells, the antibodies were first incubated with two replicates of 293T cells stably expressing human CTLA-4 at 4° C. After 30 minutes an aliquot was switched to 37° C. for 1 hour. The unbound antibodies were then washed away. After lysis with 1% Triton X 100, the anti-CTLA-4 antibodies were pulled down using protein G beads and detected by Western blot. As shown in FIG. 4A, a comparable amount of CTLA-4 protein was bound by antibodies Ab139, Ab154, Ab156-Ab159 at 4° C. After incubating at 37° C., much less CTLA-4 was associated with Ab156 and Ab157 when compared with Ab139 (TremeIgG1) or other variants with less pH sensitivity (FIG. 4B). Correspondingly, the amounts of total CTLA-4 in the cell lysate were higher in Mab156 and 157-treated cells. These data suggest that Ab156 and Ab157 dissociate from CTLA-4 when they reach inside the cells at 37° C.

To directly assess cell surface CTLA-4 levels following treatment of TremeIgG1 or its variants, CHO cells stably expressing CTLA-4 with TremeIgG1 (Ab139) or mutant antibodies Ab154 and Ab156-Ab159 were incubated either at 4° C. (no down-regulation) or 37° C. The amounts of cell surface antibody-bound CTLA-4 were measured using anti-human CTLA-4 reagents. HL12 and Ipilimumab were included as controls. As shown in FIG. 5, pre-incubation with TremeIgG1 at 37° C. caused a major reduction of cell surface CTLA-4. A similar reduction was induced by Ab154 and by Ipilimumab. Remarkably, Ab156 and Ab157, much like the non-toxic HL12, did not reduce cell surface CTLA-4. A modest reduction was induced by Ab158 and Ab159. The reduction of cell surface CTLA-4 by antibodies correlates strongly with the pH-dependence of their binding to CTLA-4 molecules (FIG. 1). These data are consistent with the hypothesis that pH-sensitivity is a good indicator for antibody-mediated reduction of cell surface anti-CTLA-4 molecules.

Example 3

Increased Antibody-Dependent Cell-Mediated Cytotoxicity (ADCC) and Anti-Tumor Activities of pH-Sensitive Anti-CTLA-4 Antibodies It has recently been demonstrated by the inventors and others that ADCC activity of anti-CTLA-4 antibodies is both necessary and sufficient to confer depletion of Treg and tumor rejection in vivo (16-18, 20). Therefore, it is of interest to assess the potential anti-tumor activity of anti-CTLA-4 antibodies using an in vitro reporter assay for ADCC activity. As shown in FIG. 6, while TremeIgG1 (Ab139) exhibits potent ADCC activity, two antibodies with the highest pH sensitivity showed even higher ADCC activity, especially at higher antibody doses.

The confirm if the ADCC reporter assay reflects selective Treg depletion in the tumor microenvironment. TremeIgG1 and Ab157 were injected into mice that received MC38 tumor cells at 14 days and had an average tumors of 7 mm in diameter. Sixteen hours later, the tumors were harvested and the % of Treg among CD4 T cells were determined by flow cytometry. As shown in FIG. 7, while TremeIgG1 was largely ineffective at this early time point, Ab157 caused significant reduction of Treg.

To test if the pH-sensitive antibodies are effective in causing tumor rejection, CTLA-$4^{h/h}$ mice were subcutaneously injected with MC38 tumor cells. Seven days later, when the tumor sizes reached about 5 mm in diameter, mice were treated with a low dose of anti-CTLA-4 mAbs, including TremeIgG1 and its pH-sensitive variants, Ab156 and Ab157. Tumor growth or recurrence was observed for 6.5 weeks (FIG. 8A). As shown in FIG. 8B-E, after three injections, TremeIgG1 caused complete tumor rejection in 80% of the mice. Remarkably, 100% rejection was achieved by Ab156 and Ab157. These data demonstrate that increased pH sensitivity improves the anti-tumor effect of anti-CTLA-4 antibodies, perhaps by increasing ADCC activity.

Figure 9:
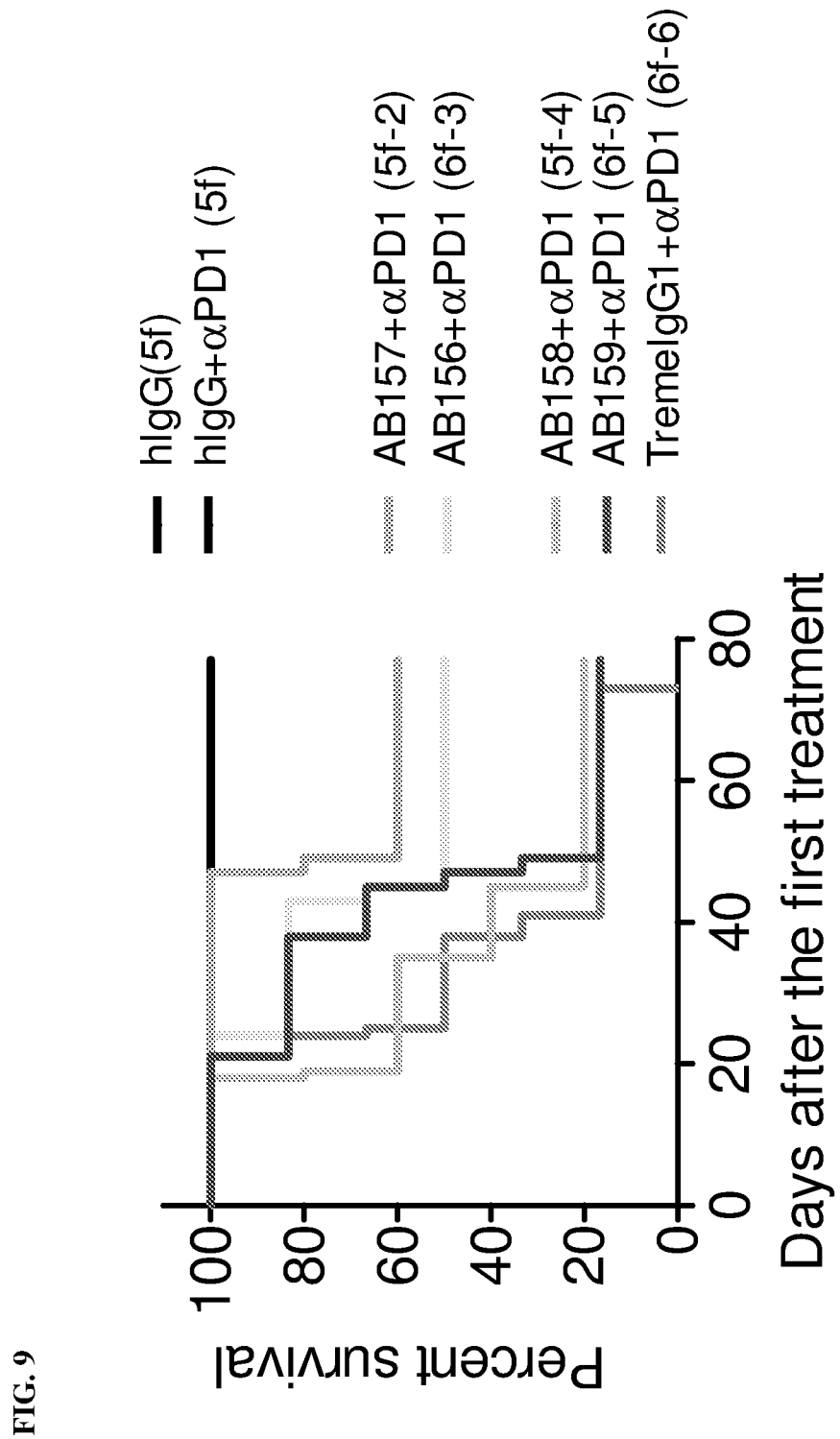
FIG. 9. pH sensitivity is associated with better safety of anti-human CTLA-4 antibodies when used in combination therapy with anti-PD-1. CTLA-4$^{h/h}$ mice received combination therapy of anti-PD-1 and one of the following anti-CTLA-4 antibodies: TremeIgG1 (AB139), AB156, AB157, AB158, AB159 on days 10, 13, 17 and 20 after birth at doses of 100 µg/mouse/injection. Safety is expressed in terms of survival over time. N=6. AB157 vs TremeIgG1, P=0.01; AB156 vs TremeIgG1, P=0.03.
Figure 10:
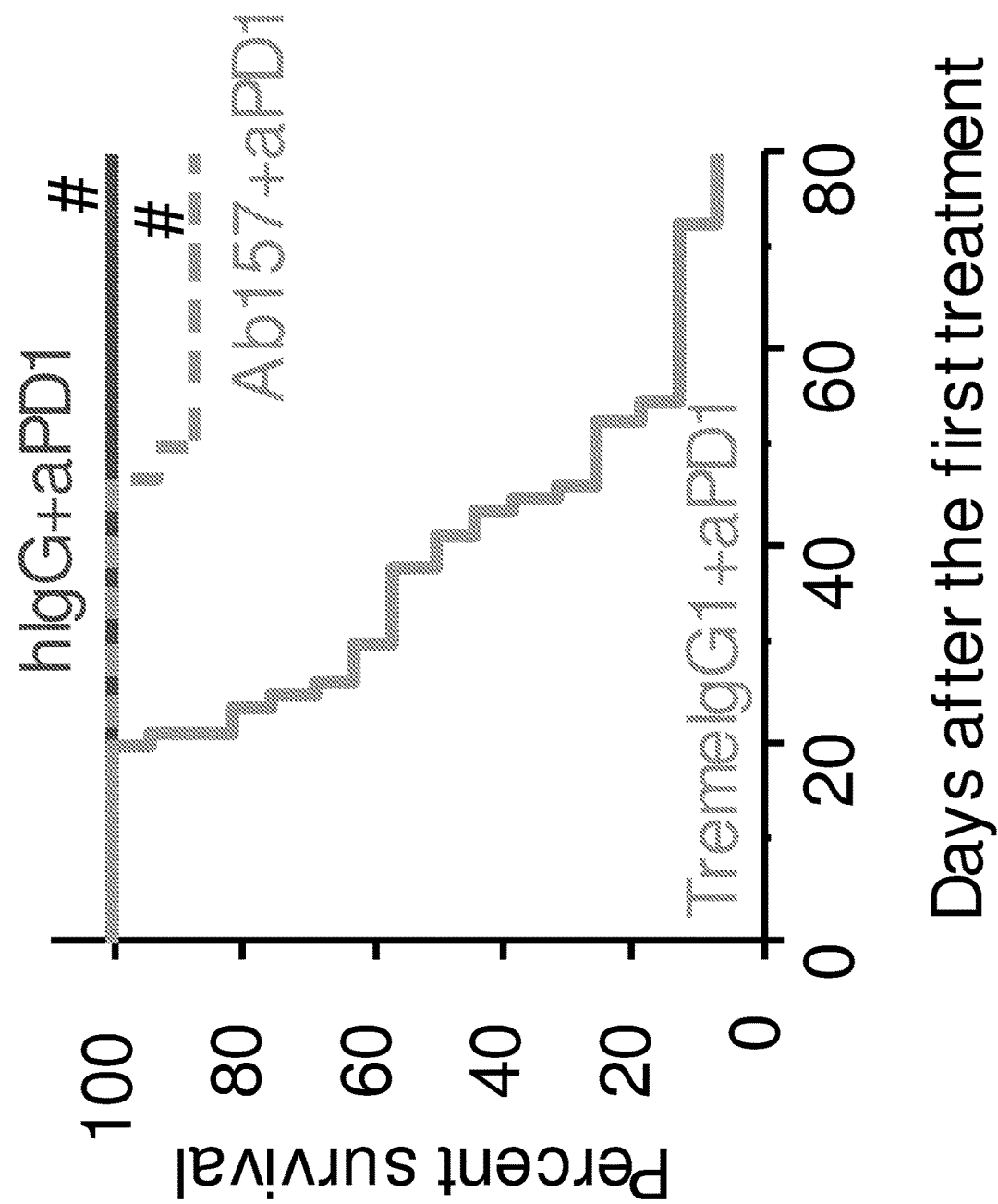
FIG. 10. Survival analysis of data from two independent experiments showing better safety of a pH-sensitive variant anti-CTLA-4 antibody, AB157, in comparison with wide-type antibody TremeIgG1. TremeIgG1 (AB139) and AB157 were administered on days 10, 13, 17 and 20 after birth at doses of 100 µg/mouse/injection. Safety is expressed in terms of survival over time. Data are a summary of two independent experiments. A statistically significant difference was observed between the two treatment groups. N=15 for AB157 or hIgGFc control+anti-PD-1, N=16 for TremeIgG1+anti-PD-1. P<0.0001.

Example 4 pH-sensitive TremeIgG1 Variants are Less Toxic than the Parent TremeIgG1 Antibody To test the impact of pH sensitivity on the toxicity of TremeIgG1 variant antibodies, mice that received either control IgG1Fc, anti-PD-1+control IgG1Fc, anti-PD-1+TremeIgG1, anti-PD-1+Ab156, or Ab157, Ab158, Ab159, starting at day 10 after birth, at doses of 100 μg/mouse/injection ×4 on days 10, 13, 17, and 20 were compared. The mice were observed for their survival. As shown in FIG. 9, while no mice receiving control IgG1Fc, or control IgG1Fc+anti-PD-1 died throughout the observation period, all but one mouse receiving TremeIgG1 died. In contrast, all but one mouse that received Ab157 survived the entire period. Significant improvement of survival was observed when Ab157 was compared with TremeIgG1 (P=0.01). Significant improvement was also observed when Ab157 was used (P=0.03). While Ab158 and Ab159 also showed somewhat better survival when compared with TremeIgG1, the difference did not reach statistically significant levels. Nevertheless, there appears to be a strong correlation between pH sensitivity and safety. When data from two experiments involving 15 mice were combined, the improvement of safety in Ab157 over TremeIgG1 is even more clearcut (FIG. 10). These data demonstrate that pH sensitivity maybe a good surrogate marker for safety of anti-CTLA-4 antibodies.

Taken together, it has been demonstrated that antibodies that retain binding to CTLA-4 at acidic pH cause reduction of cell surface CTLA-4 levels by targeting bound CTLA-4 for lysosomal degradation. As a result, these antibodies are functionally antagonist and inactivate CTLA-4 function. In vivo, such antibodies exhibit high toxicity when used in combination with anti-PD-1 antibodies. In contrast, those antibodies that lost binding to CTLA-4 at lower pH failed to reduce cell surface CTLA-4 by allowing CTLA-4 to recycle to the cell surface, and thus cannot act as agonist. Remarkably, despite their lower affinity, these antibodies appear more potent in ADCC activity and tumor rejection. These data demonstrate that increasing low pH sensitivity of anti-CTLA-4 antibodies as a novel approach to increase tumor therapeutic effect while attenuating their toxicity.

The invention claimed is:

1. An anti-CTLA-4 antibody comprising a heavy chain comprising the sequence set forth in SEQ ID NO: 3, 5, 6, 7, or 8, and a light chain comprising the sequence set forth in SEQ ID NO: 2.

2. The anti-CTLA-4 antibody of claim 1, comprising the heavy chain comprising the sequence set forth in SEQ ID NO: 6.

3. The anti-CTLA4 antibody of claim 1, comprising the heavy chain comprising the sequence set forth in SEQ ID NO: 5.

4. A method of treating a cancer in a subject in need thereof, comprising administering to the subject a cancer immunotherapy comprising the anti-CTLA-4 antibody of any one of claims 1-3, wherein the cancer is selected from the group consisting of colon cancer, liver cancer, lung cancer, kidney cancer, melanoma, prostate cancer, ovarian cancer, and pancreatic cancer.

5. The method of claim 4, wherein the anti-CTLA4-antibody is administered in combination with one or more other therapies, and wherein the one or more other therapies comprise an antibody that binds to PD-1 or PD-L1.

6. The method of claim 5, wherein the anti-PD-1 antibody is Nivolumab or Pembrolizmab.

* * * * *

SEQUENCE LISTING

```
<160> NUMBER OF SEQ ID NOS: 18

<210> SEQ ID NO 1
<211> LENGTH: 455
<212> TYPE: PRT
<213> ORGANISM: Mus musculus

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
```

```
                180                 185                 190
Val Val Thr Val Pro Ser Ser Leu Gly Thr Gln Thr Tyr Ile Cys
            195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 2
<211> LENGTH: 214
<212> TYPE: PRT
<213> ORGANISM: Mus musculus

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Tyr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95
```

```
Thr Phe Gly Pro Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 3
<211> LENGTH: 455
<212> TYPE: PRT
<213> ORGANISM: Artificial Sequence
<220> FEATURE:
<223> OTHER INFORMATION: Mutant

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His His
            20                  25                  30

Gly Met His Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240
```

-continued

Glu Leu Leu Gly Gly Pro Ser Val Phe Leu Phe Pro Lys Pro Lys
                    245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 4
<211> LENGTH: 214
<212> TYPE: PRT
<213> ORGANISM: Artificial Sequence
<220> FEATURE:
<223> OTHER INFORMATION: Mutant

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser His
            20                  25                  30

Leu His Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 5
<211> LENGTH: 455
<212> TYPE: PRT
<213> ORGANISM: Artificial Sequence
<220> FEATURE:
<223> OTHER INFORMATION: Mutant

<400> SEQUENCE: 5

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu His His His Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285
```

```
Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
450                 455

<210> SEQ ID NO 6
<211> LENGTH: 455
<212> TYPE: PRT
<213> ORGANISM: Artificial Sequence
<220> FEATURE:
<223> OTHER INFORMATION: Mutant

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr His His Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

```
Val Val Thr Val Pro Ser Ser Leu Gly Thr Gln Thr Tyr Ile Cys
            195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 7
<211> LENGTH: 455
<212> TYPE: PRT
<213> ORGANISM: Artificial Sequence
<220> FEATURE:
<223> OTHER INFORMATION: Mutant

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Asp Pro Arg Gly Ala Thr Leu Tyr His Tyr Tyr Gly Met
            100                 105                 110

Asp Val Trp Gly Gln Gly Thr Thr Val Thr Val Ser Ser Ala Ser Thr
    115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 8
<211> LENGTH: 455
<212> TYPE: PRT
<213> ORGANISM: Artificial Sequence
<220> FEATURE:
<223> OTHER INFORMATION: Mutant

<400> SEQUENCE: 8

-continued

```
Gln Val Gln Leu Val Glu Ser Gly Gly Val Gln Pro Gly Arg
1               5                   10              15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys His His Ala Asp Ser Val
        50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
```

```
                420             425             430
Cys Ser Val Met His Glu Ala Leu His Asn His Tyr Thr Gln Lys Ser
            435             440             445
Leu Ser Leu Ser Pro Gly Lys
    450             455
```

<210> SEQ ID NO 9
<211> LENGTH: 215
<212> TYPE: PRT
<213> ORGANISM: Artificial Sequence
<220> FEATURE:
<223> OTHER INFORMATION: Mutant

<400> SEQUENCE: 9

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 10
<211> LENGTH: 215
<212> TYPE: PRT
<213> ORGANISM: Artificial Sequence
<220> FEATURE:
<223> OTHER INFORMATION: Mutant

<400> SEQUENCE: 10

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

His Leu Ala Trp Tyr Gln Gln Lys Pro Gly Gln Ala Pro Arg Leu Leu
        35                  40                  45
```

```
Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
210                 215

<210> SEQ ID NO 11
<211> LENGTH: 215
<212> TYPE: PRT
<213> ORGANISM: Artificial Sequence
<220> FEATURE:
<223> OTHER INFORMATION: Mutant

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Gly Ser Ser Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190
```

-continued

```
Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 12
<211> LENGTH: 215
<212> TYPE: PRT
<213> ORGANISM: Artificial Sequence
<220> FEATURE:
<223> OTHER INFORMATION: Mutant

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

His Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 13
<211> LENGTH: 448
<212> TYPE: PRT
<213> ORGANISM: Artificial Sequence
<220> FEATURE:
<223> OTHER INFORMATION: Mutant

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60
```

-continued

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
             85                  90                  95

Ala Arg Thr Gly Trp Leu Gly Pro Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 14
<211> LENGTH: 448
<212> TYPE: PRT
<213> ORGANISM: Artificial Sequence
<220> FEATURE:

<223> OTHER INFORMATION: Mutant

<400> SEQUENCE: 14

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser His
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys His His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp His Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

Ser Asp Gly Ser Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
            435                 440                 445

<210> SEQ ID NO 15
<211> LENGTH: 448
<212> TYPE: PRT
<213> ORGANISM: Artificial Sequence
<220> FEATURE:
<223> OTHER INFORMATION: Mutant

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
            85                  90                  95

Ala Arg Thr Gly Trp Leu Gly Pro Phe Asp His Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

```
Lys Cys Lys Val Ser Asn Lys Ala Leu Pro Ala Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 16
<211> LENGTH: 448
<212> TYPE: PRT
<213> ORGANISM: Artificial Sequence
<220> FEATURE:
<223> OTHER INFORMATION: Mutant

<400> SEQUENCE: 16

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
                35                  40                  45

Thr Phe Ile Ser Tyr Asp Gly Asn Asn Lys His Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 17
<211> LENGTH: 448
<212> TYPE: PRT
<213> ORGANISM: Artificial Sequence
<220> FEATURE:
<223> OTHER INFORMATION: Mutant

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 18
<211> LENGTH: 448
<212> TYPE: PRT
<213> ORGANISM: Artificial Sequence
<220> FEATURE:
<223> OTHER INFORMATION: Mutant

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Ile Tyr Tyr Cys
                 85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```